United States Patent
Li et al.

(10) Patent No.: US 11,603,504 B2
(45) Date of Patent: Mar. 14, 2023

(54) HIGHLY FLUORINATED IONIC LIQUIDS AS BOUNDARY LUBRICANTS

(71) Applicant: UNIVERSITY OF PITTSBURGH—OF THE COMMONWEALTH SYSTEM OF HIGHER EDUCATION, Pittsburgh, PA (US)

(72) Inventors: Lei Li, Wexford, PA (US); Bingchen Wang, Pittsburgh, PA (US)

(73) Assignee: University of Pittsburgh—Of The Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 17/195,602

(22) Filed: Mar. 8, 2021

(65) Prior Publication Data

US 2021/0301216 A1     Sep. 30, 2021

Related U.S. Application Data

(60) Provisional application No. 62/986,536, filed on Mar. 6, 2020.

(51) Int. Cl.
    *C10M 105/72*     (2006.01)
    *C07D 233/60*     (2006.01)
    (Continued)

(52) U.S. Cl.
    CPC ......... *C10M 105/72* (2013.01); *C07D 233/60* (2013.01); *G11B 5/739* (2019.05);
    (Continued)

(58) Field of Classification Search
    CPC .............. C10M 105/74; C10M 105/72; C10M 105/50; C10M 105/56; C10M 2223/06;
    (Continued)

(56) References Cited

U.S. PATENT DOCUMENTS

2009/0176956 A1*   7/2009   Grinstaff .................. C07F 9/28
                                                          526/338
2017/0369807 A1*   12/2017   Kondo .................... G11B 5/725

\* cited by examiner

*Primary Examiner* — Vishal V Vasisth
(74) *Attorney, Agent, or Firm* — Paul D. Bangor, Jr., Esquire; Clark Hill PLC

(57) ABSTRACT

An ionic liquid comprising: a cation (or conjugate acid), wherein the cation (or conjugate acid) is represented by General Formula (A) below or General Formula (B) below or General Formula (C) or General Formula (D) below or General Formula (E) below:

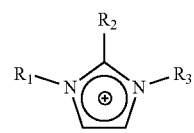

General Formula (A)

General Formula (B)

(Continued)

-continued

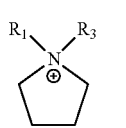

General Formula (C)

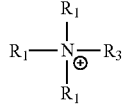

General Formula (D)

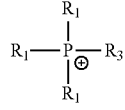

General Formula (E)

wherein $R_1$ represents $CH_2CH_2(CF_2)_nCF_3$, where n is an integer ranging from 0 to 7, or an alkyl chain $CH_3$, or $CH_2OH$, or $CH_2CH_2OH$; $R_2$ represents $CH_2CH_2(CF_2)_nCF_3$, where n is an integer ranging from 0 to 7, or a hydrogen atom H, or $CH_2OH$, or $CH_2CH_2OH$; and $R_3$ represents $CH_2CH_2(CF_2)_nCF_3$, where n is an integer ranging from 0 to 7.

8 Claims, 9 Drawing Sheets

(51) Int. Cl.
 *G11B 5/73* (2006.01)
 *C10N 20/00* (2006.01)
 *C10N 40/18* (2006.01)
(52) U.S. Cl.
 CPC ... *C10M 2219/09* (2013.01); *C10N 2020/077* (2020.05); *C10N 2040/18* (2013.01)
(58) Field of Classification Search
 CPC .......... C10M 2215/04; C10M 2219/09; C10M 2211/02; C10M 2211/00; C10M 2215/224; G11B 5/739; G11B 5/7266; C07D 233/60; C10N 2020/077; C10N 2040/18
 See application file for complete search history.

$R_1 = CH_2CH_2(CF_2)_nCF_3 (n=0-7)$
    OR $CH_3$ OR $CH_2HO$ OR $CH_2CH_2OH$
$R_2 = CH_2CH_2(CF_2)_nCF_3 (n=0-7)$
    OR H OR $CH_2HO$ OR $CH_2CH_2OH$
$R_2 = CH_2CH_2(CF_2)_nCF_3 (n=0-7)$ $R_2 = CH_2CH_2(CF_2)_nCF_3 (n=0-7)$
    OR H OR $CH_2OH$ OR $CH_2CH_2OH$
$R_3 = CH_2CH_2(CF_2)_nCF_3 (n=0-7)$ $R_1 = CH_2CH_2(CF_2)_nCF_3 (n=0-7)$
    OR $CH_3$ OR $CH_2OH$ OR $CH_2CH_2OH$
$R_3 = CH_2CH_2(CF_2)_nCF_3 (n=0-7)$ $R_1$= $CH_2CH_2(CF_2)_nCF_3$(n=0-7)
OR $CH_3$ OR $CH_2OH$ OR $CH_2CH_2OH$
$R_3$= $CH_2CH_2(CF_2)_nCF_3$ (n=0-7)

$R_1$= $CH_2CH_2(CF_2)_nCF_3$(n=0-7)
OR $CH_3$ OR $CH_2OH$ OR $CH_2CH_2OH$
$R_3$= $CH_2CH_2(CF_2)_nCF_3$ (n=0-7)

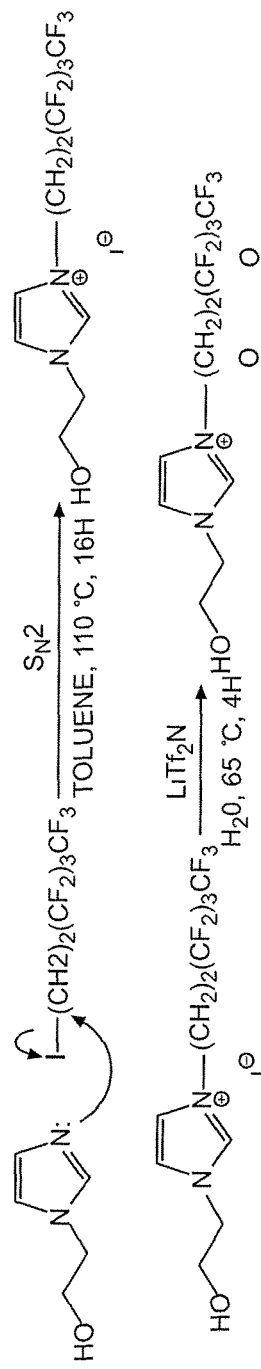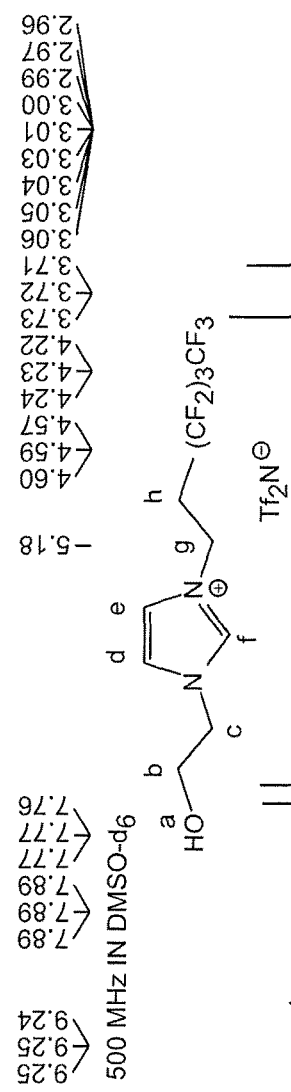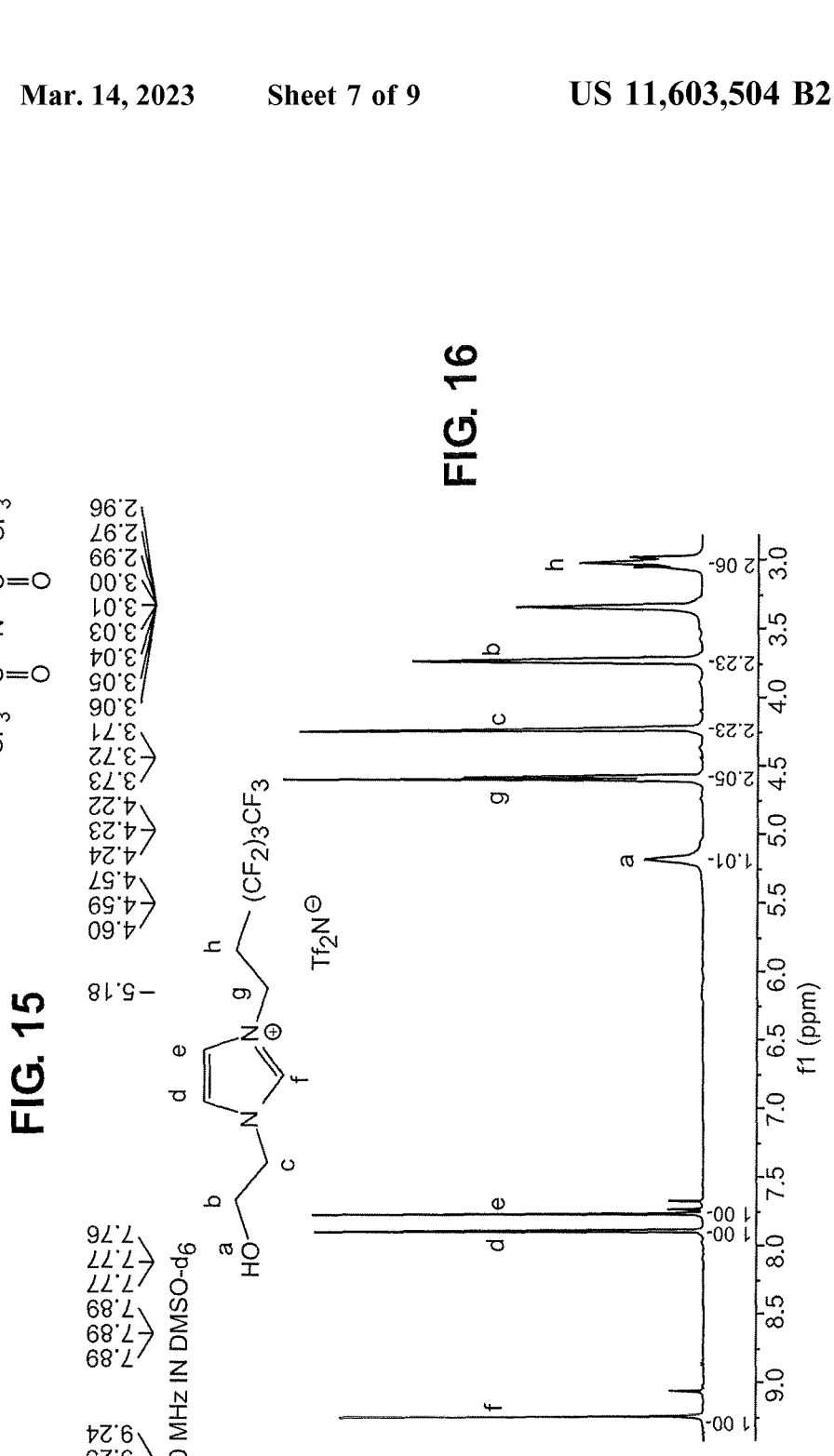
FIG. 15
FIG. 16

HIGHLY FLUORINATED IONIC LIQUIDS AS BOUNDARY LUBRICANTS

RELATED APPLICATION

This application claims priority benefit under 35 U.S.C. § 119(e) of U.S. Provisional Application No. 62/986,536 filed Mar. 6, 2020 the contents of which are herein incorporated by reference.

FIELD OF THE DISCLOSURE

Technical Field

The present disclosure relates to a group of novel highly fluorinated ionic liquids which contain cations with highly fluorinated alkyl chains and anions with multiple fluorinated components. The present disclosure also relates to methods of preparing nanometer-thick boundary lubricants containing highly fluorinated ionic liquids and the use of highly fluorinated ionic liquids as next-generation nanometer-thick boundary lubricants.

Background

The physical contact between adjacent solid surfaces has been a huge concern for many nanoscale devices with contacting components during operation, e. g., hard disc drives (HDDs) and nano-electromechanical and micro-electromechanical systems (NEMS/MEMS). The use of nanometer-thick boundary lubricants is critical to the efficiency and reliability of these devices. Ideally, the lubricants should have high thermal stability due to the increasing temperature during tribology contact, and low monolayer (ML) thickness which determines the minimum thickness of the lubricants. Additionally, the lubricants should be load-carrying and self-healing, and have low surface tension and excellent tribological property. Unfortunately, the state-of-the-art lubricant, perfluoropolyether (PFPE), only has limited thermal stability, and its ML is relatively thick due to the polymeric chain structure.

Ionic liquids (ILs) are promising candidates for the next-generation media lubricants due to their extraordinary physical properties and relatively low cost. ILs are salts that are in liquid phases at room temperature, and they consist of cations and anions. Many ILs have higher thermal stability and lower volatility over PFPEs. The molecular sizes of ILs are also much smaller than those of PFPEs, making them possible to achieve lower ML. Moreover, ILs with aromatic rings form layering structures when confined on solid surfaces, which is ideal for lubrication. Nevertheless, the major concern for conventional ILs as media lubricants is their higher surface tension than PFPEs. This drawback significantly limits the tribological performance of ILs as nanometer-thick media lubricants.

BRIEF SUMMARY OF THE DISCLOSURE

In one aspect, the present disclosure relates to the chemical compositions of a group of novel highly fluorinated ILs. The highly fluorinated ILs of the present disclosure contain cations with highly fluorinated alkyl chains and anions with multiple $CF_x$ groups, and consequently have very low surface tensions. The low surface tensions of the highly fluorinated ILs are ideal for their tribological performance.

In another aspect, the present disclosure also relates to the method of fabricating nanometer-thick lubricants that consists of highly fluorinated ILs of the present disclosure by means of a dip coating process. The thickness of the nanometer-thick lubricants can be readily controlled by changing the concentration of the bulk solution. The use of the highly fluorinated ionic liquids of the present disclosure as the next-generation nanometer-thick boundary lubricants is provided.

Many other variations are possible with the present disclosure, and those and other teachings, variations, and advantages of the present disclosure will become apparent from the description and figures of the disclosure.

A first aspect of a preferred embodiment of the present disclosure comprises an ionic liquid comprising a cation (or conjugate acid), wherein the cation (or conjugate acid) is represented by General Formula (A) below or General Formula (B) below or General Formula (C) or General Formula (D) below or General Formula (E) below:

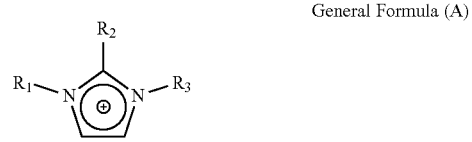

General Formula (A)

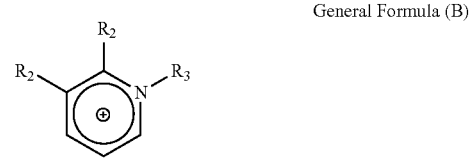

General Formula (B)

General Formula (C)

General Formula (D)

General Formula (E)

wherein $R_1$ represents $CH_2CH_2(CF_2)_nCF_3$, where n is an integer ranging from 0 to 7, or an alkyl chain $CH_3$, or $CH_2OH$, or $CH_2CH_2OH$; $R_2$ represents $CH_2CH_2(CF_2)_nCF_3$, where n is an integer ranging from 0 to 7, or a hydrogen atom H, or $CH_2OH$, or $CH_2CH_2OH$; and $R_3$ represents $CH_2CH_2(CF_2)_nCF_3$, where n is an integer ranging from 0 to 7.

A second aspect of a preferred embodiment of the present disclosure comprises an ionic liquid comprising an anion (or conjugate base) comprising bis(trifluoromethanesulfonimide), bis(nonafluorobutanesulfonyl)imide or tris(pentafluoroethyl)trifluorophosphate.

A third aspect of a preferred embodiment of the present disclosure comprises an ionic liquid comprising an anion (or conjugate base), wherein the anion (or conjugate base) is represented by General Formula (Z) below:

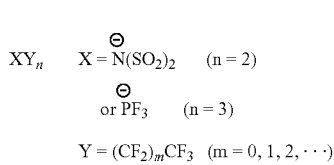

General Formula (Z)

wherein X represents $N(SO_2)_2$ with "n" equaling 2 or X represents $PF_3$ with "n" equaling 3; and wherein Y represents $(CF_2)_mCF_3$ with "m" equaling 0, 1, 2, 3, 4, 5 or 6.

A fourth aspect of a preferred embodiment of the present disclosure comprises an ionic liquid comprising a cation (or conjugate acid), wherein the cation (or conjugate acid) is represented by General Formula (A) below or General Formula (B) below or General Formula (C) or General Formula (D) below or General Formula (E):

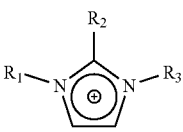

General Formula (A)

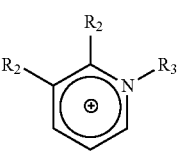

General Formula (B)

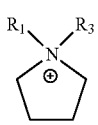

General Formula (C)

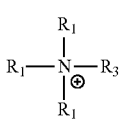

General Formula (D)

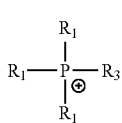

General Formula (E)

wherein $R_1$ represents $CH_2CH_2(CF_2)_nCF_3$, where n is an integer ranging from 0 to 7, or an alkyl chain $CH_3$, or $CH_2OH$, or $CH_2CH_2OH$; $R_2$ represents $CH_2CH_2(CF_2)_nCF_3$, where n is an integer ranging from 0 to 7, or a hydrogen atom H, or $CH_2OH$, or $CH_2CH_2OH$; and $R_3$ represents $CH_2CH_2(CF_2)_nCF_3$, where n is an integer ranging from 0 to 7; and an anion (or conjugate base) comprising bis(trifluoromethanesulfonimide) or bis(nonafluorobutanesulfonyl)imide or tris(pentafluoroethyl)trifluorophosphate or an anion (or conjugate base), wherein the anion (or conjugate base) is represented by General Formula (Z) below:

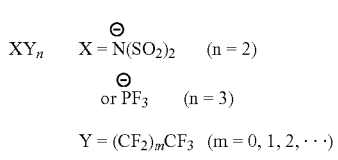

General Formula (Z)

wherein X represents $N(SO_2)_2$ with "n" equaling 2 or X represents $PF_3$ with "n" equaling 3; and wherein Y represents $(CF_2)_mCF_3$ with "m" equaling 0, 1, 2, 3, 4, 5 or 6.

An additional aspect of a preferred embodiment of the present disclosure comprises a lubricant comprising the ionic liquid according to the first aspect above.

A further aspect of a preferred embodiment of the present disclosure comprises a lubricant comprising the ionic liquid according to the second aspect above.

Another aspect of a preferred embodiment of the present disclosure comprises a lubricant comprising the ionic liquid according to the third aspect above.

An additional aspect of a preferred embodiment of the present disclosure comprises a lubricant comprising the ionic liquid according to the fourth aspect above.

Yet another aspect of a preferred embodiment of the present disclosure comprises a magnetic recording medium comprising a non-magnetic support; a magnetic layer on the non-magnetic support; and the lubricant according to the first aspect above on the magnetic layer.

In another aspect of a preferred recording medium of the present disclosure, the magnetic layer has a carbon overcoat and the lubricant is disposed on the carbon overcoat of the magnetic layer.

Another aspect of a preferred embodiment of the present disclosure comprises a method of applying an ionic liquid on a surface of a solid substrate, such as a magnetic media with a carbon overcoat, comprising preparing a dilute solution by dissolving the ionic liquid in 2,3-dihydrodecafluoropentane; dipping the solid substrate into the dilute solution vertically at a first rate of travel (mm/min); and withdrawing the solid substrate vertically from the dilute solution at a second rate of travel (mm/min).

In another aspect of a preferred method of applying an ionic liquid on a surface of a solid substrate of the present disclosure, the first rate of travel equals the second rate of travel.

In yet another aspect of a preferred method of applying an ionic liquid on a surface of a solid substrate of the present disclosure, each of the first rate of travel and the second rate of travel equals 60 mm/min.

In a further aspect of a preferred method of applying an ionic liquid on a surface of a solid substrate of the present disclosure, the first rate of travel is not equal to the second rate of travel.

Another aspect of a preferred embodiment of the present disclosure comprises a method for making a fluorinated ionic liquid, comprising dissolving iodide of $CH_2CH_2(CF_2)_nCF_3$ (n=0-7) in Toluene to produce a first solution; mixing and/or combining a starting material with the first solution to produce a first reaction, wherein the starting material is represented by General Formula (F) below or General Formula (G) below or General Formula (H) or General Formula (I) below or General Formula (J):

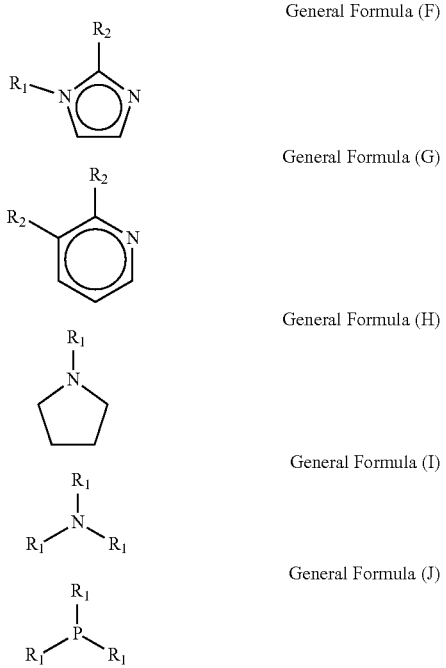

General Formula (F)

General Formula (G)

General Formula (H)

General Formula (I)

General Formula (J)

wherein $R_1$ represents $CH_2CH_2(CF_2)_nCF_3$, where n is an integer ranging from 0 to 7, or an alkyl chain $CH_3$, or $CH_2OH$, or $CH_2CH_2OH$; $R_2$ represents $CH_2CH_2(CF_2)_nCF_3$, where n is an integer ranging from 0 to 7, or a hydrogen atom H, or $CH_2OH$, or $CH_2CH_2OH$; stirring and refluxing the first reaction at 110° C. under $N_2$ purging for 15 hours; cooling the stirred and refluxed first reaction to room temperature; decanting Toluene from the first reaction to produce a remainder product; stirring the remainder product in diethyl ether; washing the remainder product with diethyl ether a plurality of times; drying the washed remainder product under a vacuum overnight; dissolving the dried remainder product in water at 65° C. to produce a second solution; adding a fluorinated anion to the second solution to produce a metathesis reaction, wherein the fluorinated anion is an anion (or conjugate base) comprising bis(trifluoromethanesulfonimide) or bis(nonafluorobutanesulfonyl)imide or tris(pentafluoroethyl)trifluorophosphate or an anion (or conjugate base), wherein the anion (or conjugate base) is represented by General Formula (Z) below:

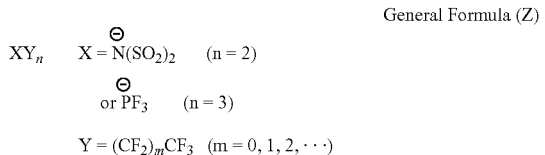

General Formula (Z)

wherein X represents $N(SO_2)_2$ with "n" equaling 2 or X represents $PF_3$ with "n" equaling 3; and wherein Y represents $(CF_2)_mCF_3$ with "m" equaling 0, 1, 2, 3, 4, 5 or 6; stirring the metathesis reaction for 3 to 4 hours; dissolving the stirred metathesis reaction product in ethyl acetate to produce a third solution; washing the third solution with DI water until its pH 6-7; testing the washed third solution of pH 6-7 on I" with $AgNO_3$ in a separated water phase to confirm test is negative; performing rotary evaporation on the washed and tested third solution to extract a final product; and drying the final product in a vacuum at 75° C. overnight to produce the fluorinated ionic liquid.

BRIEF DESCRIPTION OF THE DRAWINGS

The present disclosure is illustrated by way of example and not limitation in the figures of the accompanying drawings, in which:

FIG. 15 shows a preferred reaction sequence for the synthesis of 1-1H,1H,2H,2H-perfluorohexyl-3-2-hydroxylethylimidazolium bis(trifluoromethylsulfonyl)imide according to a preferred method of the present disclosure;

FIG. 16 shows a $^1$H NMR spectrum of 1-1H,1H,2H,2H-perfluorohexyl-3-2-hydroxyethylimidazolium bis(trifluoromethylsulfonyl)imide synthesized according to a preferred method of the present disclosure;

DETAILED DESCRIPTION OF PREFERRED EMBODIMENTS

Figure 1:
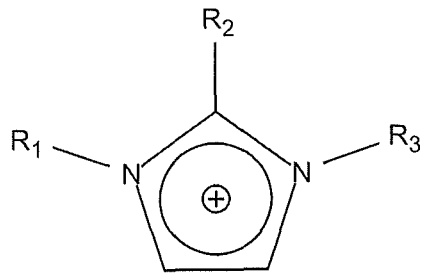
FIG. 1 shows preferred chemical structures of the imidazolium cations in the highly fluorinated ILs of the present disclosure.

The following description, taken in conjunction with the referenced drawings, is presented to enable one of ordinary skill in the art to make and use the disclosure and to incorporate it in the context of particular applications. Various modifications, as well as a variety of uses in different applications, will be readily apparent to those skilled in the art, and the general principles, defined herein, may be applied to a wide range of aspects. The present disclosure is not intended to be limited to the aspects disclosed herein. Instead, it is to be afforded the widest scope consistent with the disclosed aspects.

In HDDs, nanometer-thick lubricants need to be applied on the media surfaces in order to reduce direct head-media contact and protect the media from wear during operations. In NEMS/MEMS, it is desirable to have ultrathin anti-adhesive coatings on the surfaces of the nanoscale/microscale devices to avoid device breakdown. ILs have huge potential to be the next-generation lubricants in those devices because of their small molecular sizes, excellent tribological properties, high thermal stability, negligible volatility, and low cost. More specifically, the lubricant thickness can be reduced due to the small molecular size of ILs, and the lubricant thermal stability can be enhanced due to the strong electrostatic interactions between the cations and the anions. Another key characteristic of such IL boundary lubrication is the low friction, which is largely determined by the surface tension of the IL molecules. The surface tensions of the conventional commercially available ILs (>30 mN/m in general), however, is higher than that of the state-of-the-art PFPE lubricants (e. g., 24 mN/m for PFPE Zdol), which leads to higher frictions of the IL lubricants than the PFPE lubricants. The relatively high surface tensions of the current ILs significantly limit their tribological performance.

To address the current issue, the present disclosure relates to the chemical compositions of novel highly fluorinated IL molecules and the method to apply the highly fluorinated IL lubricants on solid surfaces, e. g., the surfaces of magnetic media. For the molecular design of the next-generation IL lubricants, it is necessary to add multiple $CF_x$ groups in both the cations and the anions of the IL molecules to achieve lower surface tensions and better tribological performance, as the strong C—F bonds and the low polarity in the fluorinated components can lead to weak intermolecular forces, and consequently low surface tensions. Preferably, the IL molecules of the present disclosure contain enough fluorinated components so as to have low surface tensions that are comparable to the surface tensions of PFPEs, which can result in much more robust tribological properties than the current ILs. The chemical structures of both the highly fluorinated cations and the highly fluorinated anions have been provided in the present disclosure. The highly fluorinated IL molecules can be random combinations of the preferred cations and anions of the present disclosure set forth below.

FIG. 1 illustrates the preferred chemical structures of the imidazolium cations of the highly fluorinated ILs of the present disclosure. In FIG. 1, the IL cation contains an imidazolium ring with multiple side chains. The side chain $R_1$ on the nitrogen atom N represents either $CH_2CH_2(CF_2)_nCF_3$, where n is an integer ranging from 0 to 7, or an alkyl chain $CH_3$, or $CH_2OH$, or $CH_2CH_2OH$. —OH functional groups will provide bonding between the IL and the solid substrate, e.g., magnetic media with carbon overcoat (COC). The side chain $R_2$ on the carbon atom C represents either $CH_2CH_2(CF_2)_{11}CF_3$, where n is an integer ranging from 0 to 7, or a hydrogen atom H, or $CH_2OH$, or $CH_2CH_2OH$. The side chain $R_3$ on the other nitrogen atom N represents $CH_2CH_2(CF_2)_nCF_3$, where n is an integer ranging from 0 to 7.

Figure 2:
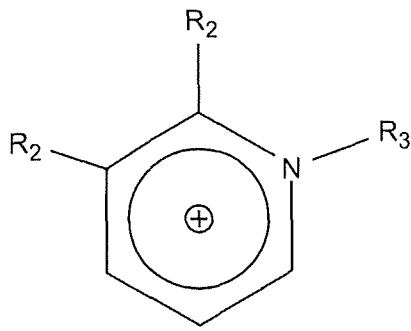
FIG. 2 shows preferred chemical structures of the pyridinium cations in the highly fluorinated ILs of the present disclosure.

FIG. 2 illustrates the chemical structures of the pyridinium cations of the highly fluorinated ILs of the present disclosure. In FIG. 2, the IL cation contains a pyridinium ring with multiple side chains. The two side chains $R_2$ on the carbon atoms C represents either $CH_2CH_2(CF_2)_nCF_3$, where n is an integer ranging from 0 to 7, or a hydrogen atom H, or $CH_2OH$, or $CH_2CH_2OH$. —OH functional groups will provide bonding between the IL and the solid substrate, e.g., magnetic media with COC. The two side chains $R_2$ can be either identical or different. The side chain $R_3$ on the nitrogen atom N represents $CH_2CH_2(CF_2)_nCF_3$, where n is an integer ranging from 0 to 7.

Figure 3:
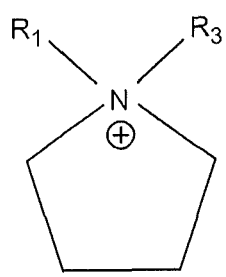
FIG. 3 shows preferred chemical structures of the pyrrolidinium cations in the highly fluorinated ILs of the present disclosure.

FIG. 3 illustrates the chemical structures of the pyrrolidinium cations of the highly fluorinated ILs of the present disclosure. In FIG. 3, the IL cation contains a pyrrolidinium ring with two side chains on the nitrogen atom N. The side chain $R_1$ represents either $CH_2CH_2(CF_2)_nCF_3$, where n is an integer ranging from 0 to 7, or an alkyl chain $CH_3$, or $CH_2OH$, or $CH_2CH_2OH$. —OH functional groups will provide bonding between the IL and the solid substrate, e.g., magnetic media with COC. The other side chain $R_3$ represents $CH_2CH_2(CF_2)_nCF_3$, where n is an integer ranging from 0 to 7.

Figure 4:
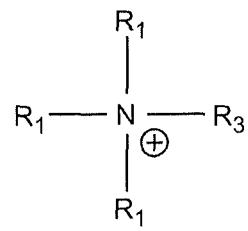
FIG. 4 shows preferred chemical structures of the ammonium cations in the highly fluorinated ILs of the present disclosure.

FIG. 4 illustrates the chemical structures of the ammonium cations of the highly fluorinated ILs of the present disclosure. In FIG. 4, the IL cation contains an ammonium structure with four side chains on the nitrogen atom N. The three side chains $R_1$ represents either $CH_2CH_2(CF_2)_nCF_3$, where n is an integer ranging from 0 to 7, or an alkyl chain $CH_3$, or $CH_2OH$, or $CH_2CH_2OH$. —OH functional groups will provide bonding between the IL and the solid substrate, e.g., magnetic media with COC. The three side chains $R_1$ can be either identical or different. The side chain $R_3$ represents $CH_2CH_2(CF_2)_nCF_3$, where n is an integer ranging from 0 to 7.

Figure 5:
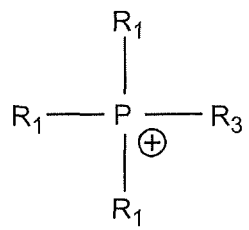
FIG. 5 shows preferred chemical structures of the phosphonium cations in the highly fluorinated ILs of the present disclosure.

FIG. 5 illustrates the chemical structures of the phosphonium cations of the highly fluorinated ILs of the present disclosure. In FIG. 5, the IL cation contains a phosphonium structure with four side chains on the nitrogen atom N. The three side chains $R_1$ represents either $CH_2CH_2(CF_2)_nCF_3$, where n is an integer ranging from 0 to 7, or an alkyl chain $CH_3$, or $CH_2OH$, or $CH_2CH_2OH$. —OH functional groups will provide bonding between the IL and the solid substrate, e.g., magnetic media with COC. The three side chains $R_1$ can be either identical or different. The side chain $R_3$ represents $CH_2CH_2(CF_2)_nCF_3$, where n is an integer ranging from 0 to 7.

Figure 6A:
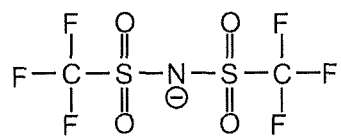
FIG. 6A shows a preferred chemical structure of an anion in the highly fluorinated ILs of the present disclosure.
Figure 6B:
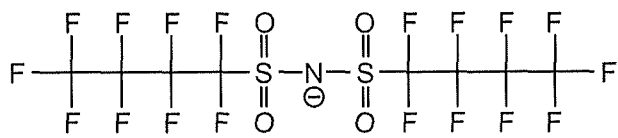
FIG. 6B shows a preferred chemical structure of another anion in the highly fluorinated ILs of the present disclosure.
Figure 6C:
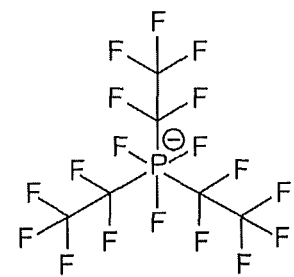
FIG. 6C shows a preferred chemical structure of yet another anion in the highly fluorinated ILs of the present disclosure.

FIGS. 6(a)-(c) illustrates the chemical structures of the anions of the highly fluorinated ILs of the present disclosure. All of the anions are hydrophobic with sufficient fluorinated components. In FIG. 6(a), the anion is bis(trifluoromethanesulfonimide). In FIG. 6(b), the anion is bis(nonafluorobutanesulfonyl)imide with more fluorinated components than bis(trifluoromethanesulfonimide). In FIG. 6(c), the anion is tris(pentafluoroethyl)trifluorophosphate, which has even more fluorinated components than bis(nonafluorobutanesulfonyl)imide.

Figure 7:
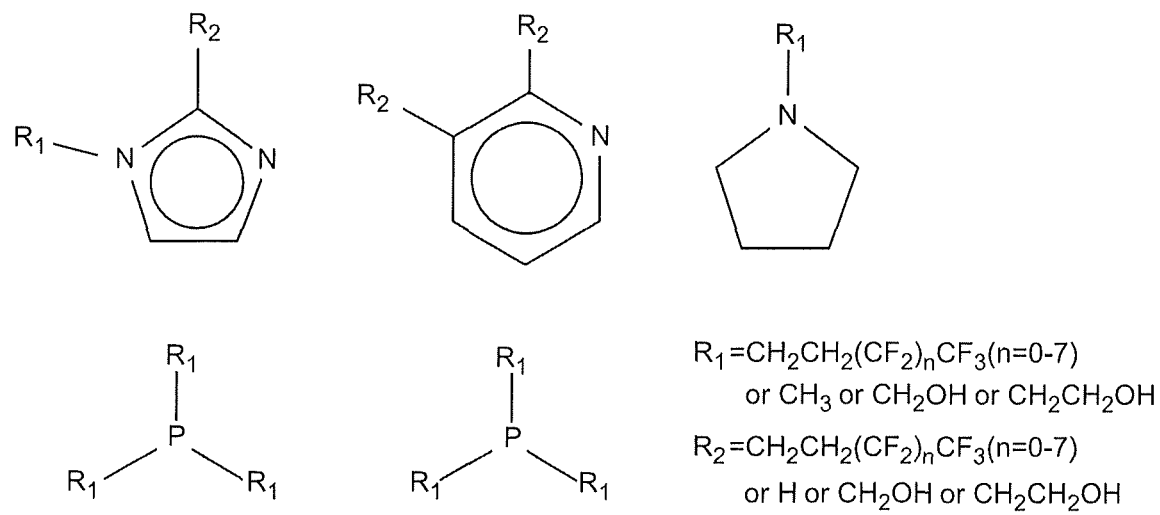
FIG. 7 shows preferred chemical structures of the starting compounds for the synthesis of the highly fluorinated ILs of the present disclosure.

The highly fluorinated ILs of the present disclosure are obtained by a two-step synthesis described herein. The first step of the synthesis undergoes a $S_N2$ reaction, where the highly fluorinated alkyl chain, i.e., the side chain $R_3$, is added in the cation. As shown in FIG. 7, the starting compound in the present disclosure can be an imidazole with side chains $R_1$ and $R_2$ on the ring, or a pyridine with two $R_2$ side chains on the ring, or a pyrrolidine with the $R_1$ side chain on the nitrogen atom N, or an amine with three $R_1$ side chains on the nitrogen atom N, or a phosphine with three $R_1$ side chains on the phosphorus atom P. Initially, the iodide of $CH_2CH_2(CF_2)_nCF_3$ is dissolved in Toluene. The starting material is added in the solution, and the reaction is stirred and refluxed at 110° C. under $N_2$ purging for 15 hr. After cooling to room temperature (RT), Toluene is decanted. The remaining product is stirred in diethyl ether, washed with diethyl ether for several times, and dried under vacuum overnight. The second step of the synthesis undergoes a metathesis reaction, where the highly fluorinated anion replaces the iodide anion. The product from the first step is dissolved in water at 65° C. The highly fluorinated anions in the present disclosure in the form of the lithium salt or the sodium salt is then added, and the reaction is stirred for 3-4 hours. After the metathesis reaction, the product is dissolved in ethyl acetate and washed with DI water until pH 6-7. The test on F with $AgNO_3$ in the separated water phase is negative. Finally, the final product is obtained after rotary evaporation and vacuum drying at 75° C. overnight.

Figure 8:
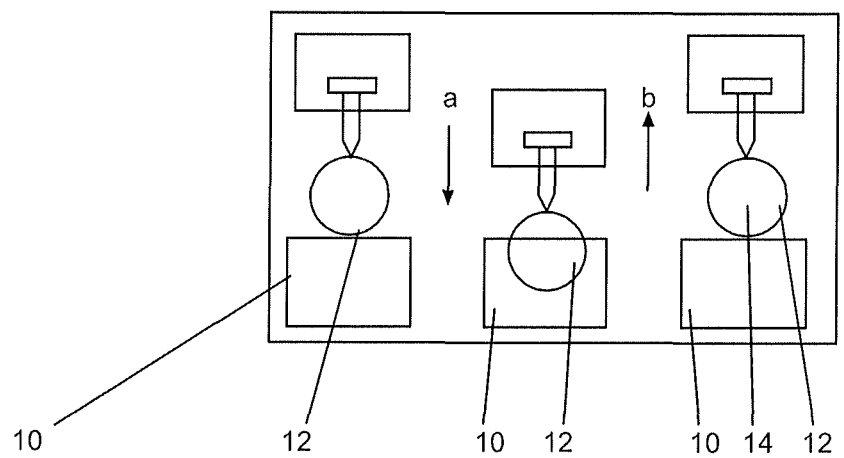
FIG. 8 is a schematic diagram showing fabrication of the nanometer-thick films composed of the highly fluorinated ILs according to preferred methods of the present disclosure.

FIG. 8 shows a preferred method of the present disclosure of applying the highly fluorinated IL lubricants on the surfaces of solid substrates, such as the magnetic media with COC, by dip coating. First, dilute solutions 10 are made by dissolving the highly fluorinated ILs in 2,3-dihydrodecafluoropentane, (commercially known as Vertrel XF), which can be obtained from Miller-Stephenson Chemical Company. The highly fluorinated ILs easily dissolve in the solvent. The solid substrate 12 is then dipped into the solution 10 vertically at a preferred first rate of travel "a" of about 60 mm/min and withdrawn vertically at a second rate of travel "b" which preferably may be the same or different from the first rate of travel "a". The solvent then evaporates immediately, leaving behind a smooth nanometer-thick film 14 of the highly fluorinated ILs. The lubricant films made of highly fluorinated ILs having low surface tensions according to the present disclosure. Based on various lubrication requirements in static/sliding friction, anti-wear, anti-adhesion, and lubricant thickness, the film thickness can be precisely controlled by changing the concentrations of the solutions. For example, lubricant films with sub-ML thickness can be fabricated from more diluted solutions, and lubricant films with thickness of several MLs can be fabricated from more concentrated solutions.

The highly fluorinated ILs of the present disclosure are designed to be the next-generation nanometer-thick boundary lubricants, which preferably are fabricated by means of the dip coating method described herein with reference to FIG. 8. The ML thicknesses are reduced compared to the current media lubricants due to their small molecular sizes. Their tribological performances are improved compared to the current IL lubricants because of their more fluorinated components in the molecular structures and their lower surface tensions. Moreover, the layering structure of the solid-confined highly fluorinated ILs is ideal for lubrication. The highly fluorinated ILs of the present disclosure form layering of cations and anions on charged solid surfaces, e. g., the surfaces of silicon wafer and mica. Highly fluorinated ILs of the present disclosure with aromatic rings in the cations also form layering structures with enhanced packing efficiency on the surfaces of amorphous carbon with $sp^2$ hybridization, i.e., COC, graphene, and graphite. In addition to the use as media lubricants, the nanometer-thick highly fluorinated ILs are also designed for many other applications, e. g., the ultrathin anti-adhesive coatings in NEMS/MEMS.

EXAMPLES

The present disclosure includes is not limited to the present examples. In the presented examples, the highly fluorinated ionic liquids were synthesized and characterized. The nanometer-thick lubricants consisting of the highly fluorinated ILs were fabricated, and then the ML thickness and friction were presented.

Thermogravimetric analysis (TGA) was performed to determine the thermal stability of the highly fluorinated ILs. These tests were conducted with a SEIKO-220 TG system, using sample weight of ~25 mg. The samples were heated from room temperature to 600° C. at a heating rate of 10° C./min in 94% $N_2$/6% $O_2$.

The substrate used is COC, on which the nanometer-thick lubricants are applied in the HDDs. Thicknesses of the nanometer-thick lubricants were measured with an Alpha-SE (J. A. Woollam Co.) spectroscopic ellipsometer. The incident angle was 70° and the wavelength range was 380-900 nm.

AFM imaging was conducted to investigate the surface roughness of the nanometer-thick lubricants on COC. The scans were performed at tapping mode with a Veeco Dimension V Scanning Probe Microscope (256 by 256 pixels, 0.1 nm vertical resolution). The AFM probe utilized has an aluminum tip on a n-type silicon cantilever (MikroMasch NSC14/AL BS, 160 kHz resonance frequency, 5.0 N/m force constant, 8 nm tip radius). The scan size was 10 μm by 10 μM for all scans, which determined the lateral resolution of 39 nm at 256 pixels.

Tribology testing was performed with a CSM Instruments Nanotribometer ($NTR^2$) on top of a Kinetic Systems anti-vibration platform. Friction force and normal force were measured with a dual beam cantilever and high-resolution capacitive sensors. The counterface used was a 2 mm diameter stainless steel sphere. The normal load was 10 mN, the maximum linear speed was 0.20 cm/s, the half amplitude was 1.00 mm, and 50 cycles were performed. The tests were conducted at 20-22° C. and 6-50% relative humidity.

To understand the bonding interactions between the highly fluorinated ILs and COC, the coated media was washed with pure Vertrel XF with a procedure similar to dip coating as described herein with reference to FIG. 8. During this procedure, the coated media was dipped into and withdrawn from the solvent at 60 mm/min. The thicknesses of the remaining lubricants on COC were then determined by ellipsometry.

Example 1

Figure 9:
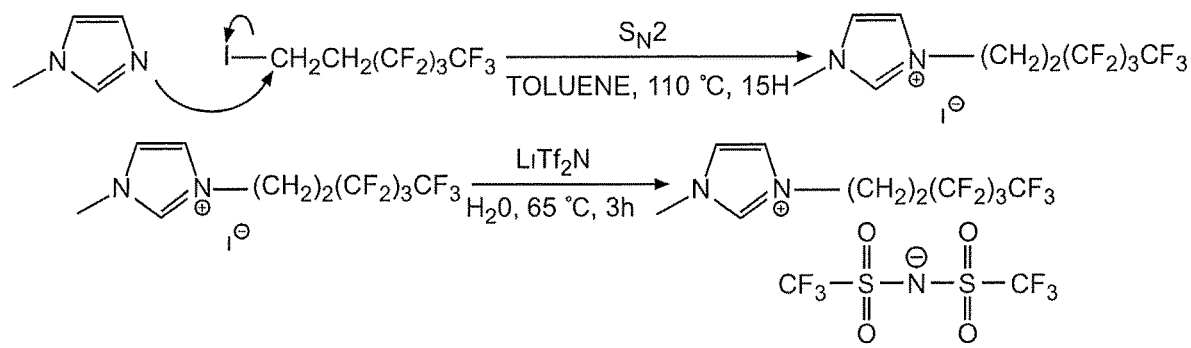
FIG. 9 shows a preferred reaction sequence for the synthesis of 1-1H,1H,2H,2H-perfluorohexyl-3-methylimidazolium bis(trifluoromethylsulfonyl)imide according to a preferred method of the present disclosure.

FIG. 9 illustrates the synthetic path of 1-1H,1H,2H,2H-perfluorohexyl-3-methylimidazolium bis(trifluoromethylsulfonyl)imide. Initially, 21.8 mmol 1-Iodo-1H,1H,2H,2H-perfluorohexane was dissolved in 35 mL Toluene. 24.0 mmol 1-methylimidazole was added, and the reaction is refluxed at 110° C. under $N_2$ purging for 15 hr. The first step of the synthesis undergoes a $S_N2$ reaction. After cooling to RT, Toluene was decanted. The remaining wax was stirred in 200 mL diethyl ether. The wax was washed with 2×150 mL diethyl ether and dried under vacuum overnight. The solid product was then dissolved in 80 mL DI water at 65° C. 21.8 mmol lithium bis(trifluoromethane)sulfonimidate was then added, and the reaction was stirred for 3 hr. The second step of the synthesis undergoes a metathesis reaction. Afterwards, the product was dissolved in 200 mL ethyl acetate and washed with 4×100 mL DI water until pH 6-7. The test on I" with $AgNO_3$ in the separated water phase was negative. Finally, the final product was extracted from the solvent by rotary evaporation and dried under vacuum at 75° C. overnight. The obtained 1-1H,1H,2H,2H-perfluorohexyl-3-methylimidazolium bis(trifluoromethylsulfonyl)imide was a viscous liquid.

Figure 10:
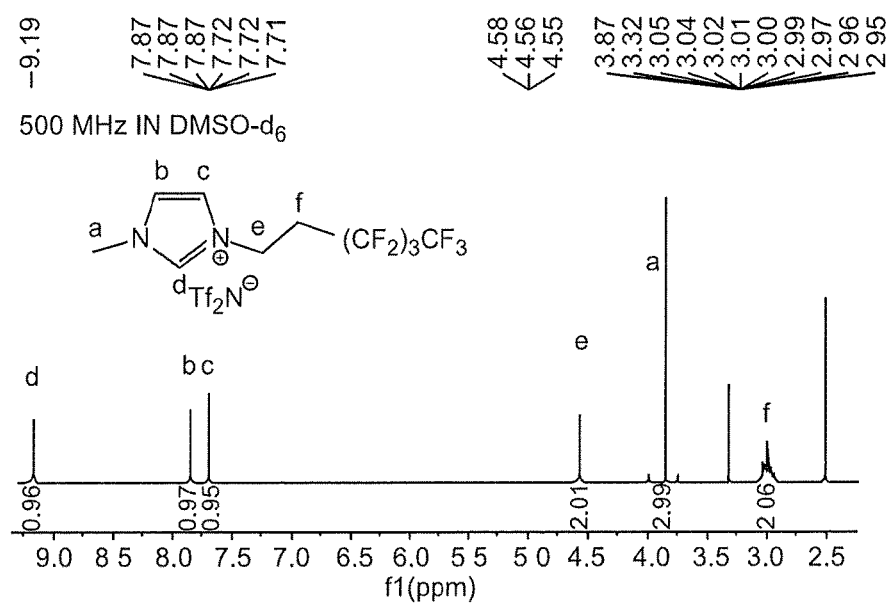
FIG. 10 shows a $^1H$ NMR spectrum of 1-1H,1H,2H,2H-perfluorohexyl-3-methylimidazolium bis(trifluoromethylsulfonyl)imide synthesized according to a preferred method of the present disclosure.
Figure 11:
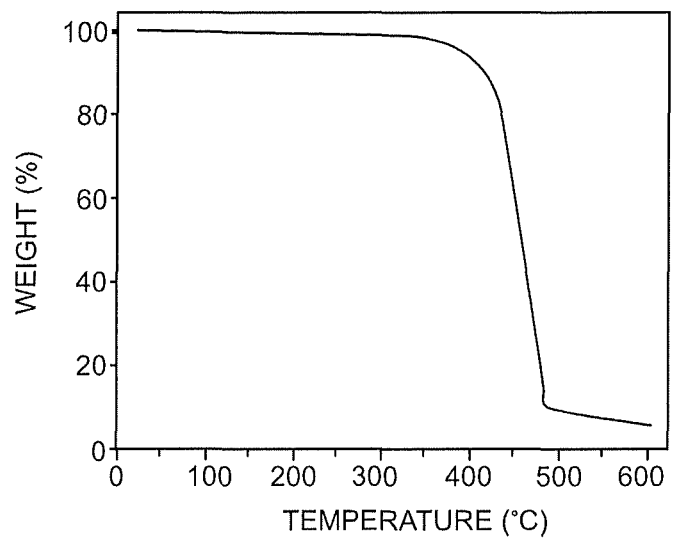
FIG. 11 shows TGA results of 1-1H,1H,2H,2H-perfluorohexyl-3-methylimidazolium bis(trifluoromethylsulfonyl)imide synthesized according to a preferred method of the present disclosure.

$^1$H NMR was conducted on the synthesized 1-1H,1H,2H,2H-perfluorohexyl-3-methylimidazolium bis(trifluoromethylsulfonyl)imide. The spectrum and all the peak assignments are indicated in FIG. 10, which demonstrates the successful synthesis. The peak at 2.5 ppm is from the trace impurities of the solvent DMSO-$d_6$, and the peak at 3.3 ppm is from absorbed water in the solvent. Additionally, as shown in FIG. 11, only one step of weight loss can be detected by TGA, which further demonstrates the high purity of the product. The TGA result also indicates the excellent thermal stability of the product. The surface tension of the highly fluorinated IL reduces to 24.5 mN/m based on the pendant drop analysis, as compared to the 30.8 mN/m surface tension for the commercially available 1-hexyl-3-methylimidazolium bis(trifluoromethylsulfonyl)imide.

Figure 12:
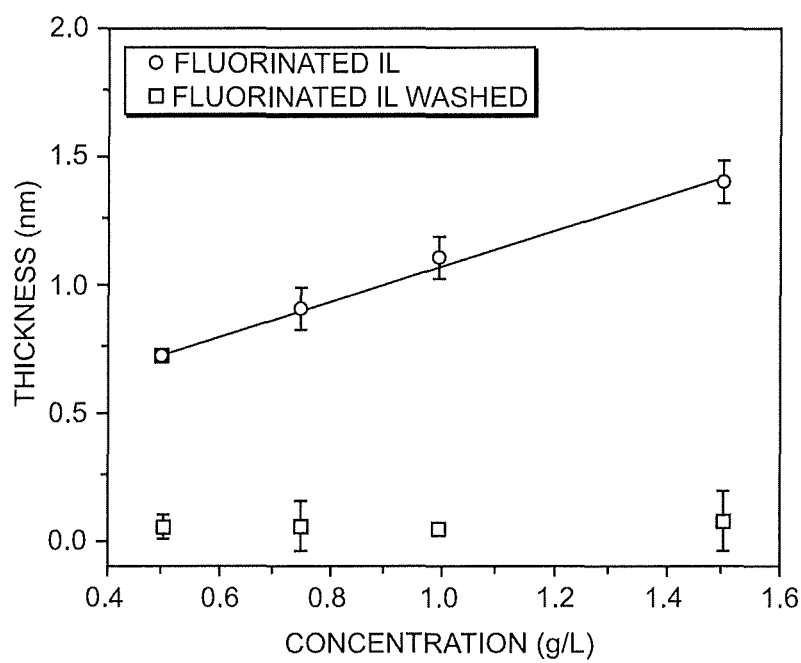
FIG. 12 shows nanofilm thicknesses of 1-1H,1H,2H,2H-perfluorohexyl-3-methylimidazolium bis(trifluoromethylsulfonyl)imide on carbon overcoat (COC) at various concentrations before and after Vertrel XF washing according to preferred methods of the present disclosure.

Nanometer-thick lubricants consisting of 1-1H,1H,2H,2H-perfluorohexyl-3-methylimidazolium bis(trifluoromethylsulfonyl)imide was applied on the COC surfaces by the preferred fabrication method of the current disclosure. As shown in FIG. 12, the thickness of the fabricated nanofilms increases proportionally with the concentration of the bulk solutions within the investigated thickness range of nanofilm thickness. FIG. 12 also shows that most of the nanofilms of the highly fluorinated IL of the present disclosure can be washed off the COC surfaces by Vertrel XF, indicating weak bonding of the nanofilms to the solid substrates.

Figure 13:
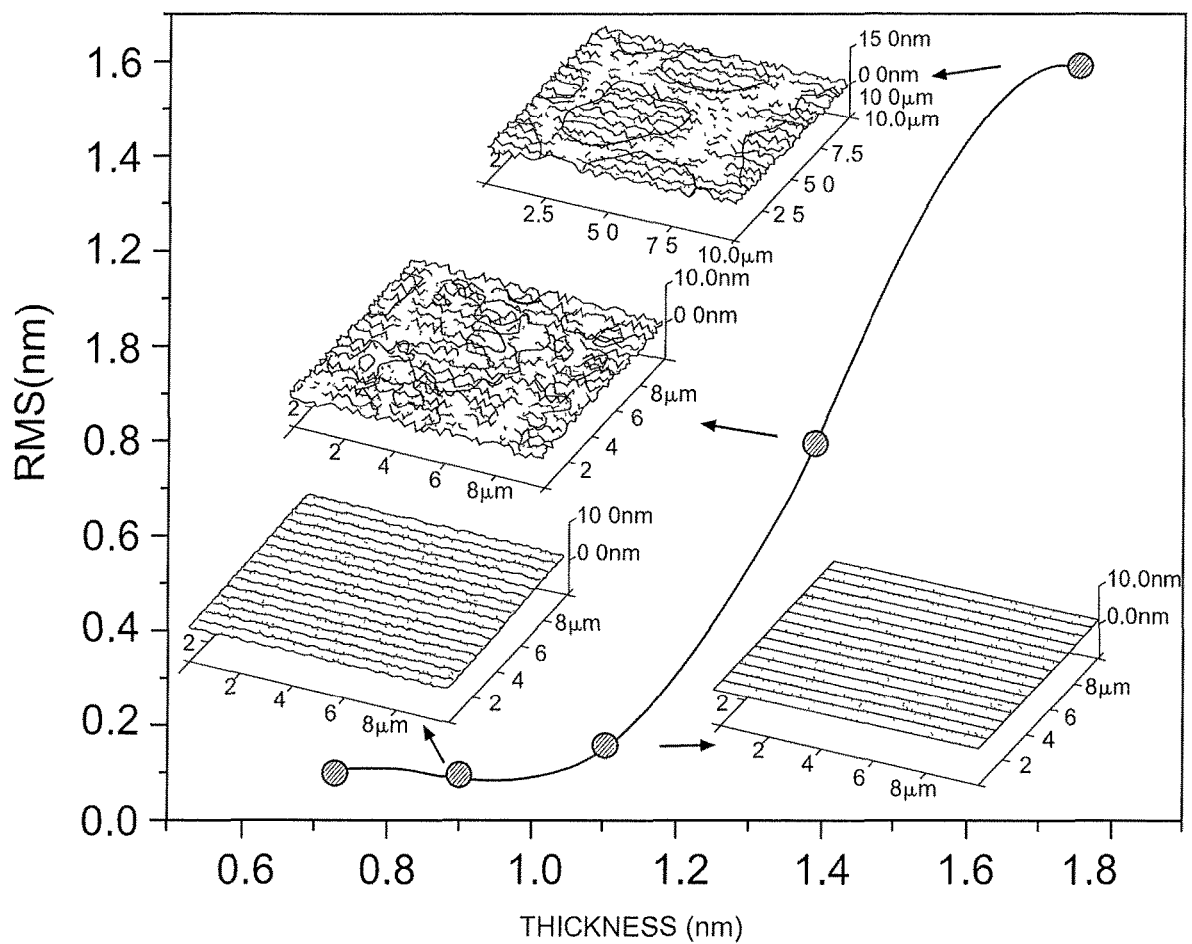
FIG. 13 shows surface roughness results of the nanometer-thick perfluorohexyl-3-methylimidazolium bis(trifluoromethylsulfonyl)imide with varying thicknesses on COC according to preferred methods of the present disclosure.

ML thickness of the synthesized 1-1H,1H,2H,2H-perfluorohexyl-3-methylimidazolium bis(trifluoromethylsulfonyl)imide was determined by AFM surface roughness analysis. FIG. 13 shows the surface roughness results (represented by the root-mean-square roughness, RMS) and the corresponding AFM images of the highly fluorinated IL with different thicknesses on COC. The AFM roughness results revealed that the surfaces remained very smooth for nanofilms thinner than ~0.9 nm, while the surfaces became much rougher for the nanofilms thicker than ~0.9 nm. Therefore, 0.9 nm is determined to be the ML thickness of 1-1H,1H,2H,2H-perfluorohexyl-3-methylimidazolium bis(trifluoromethylsulfonyl)imide. The small molecular size of the highly fluorinated IL of the present disclosure determines the extremely low ML thickness of the nanofilms.

Figure 14:
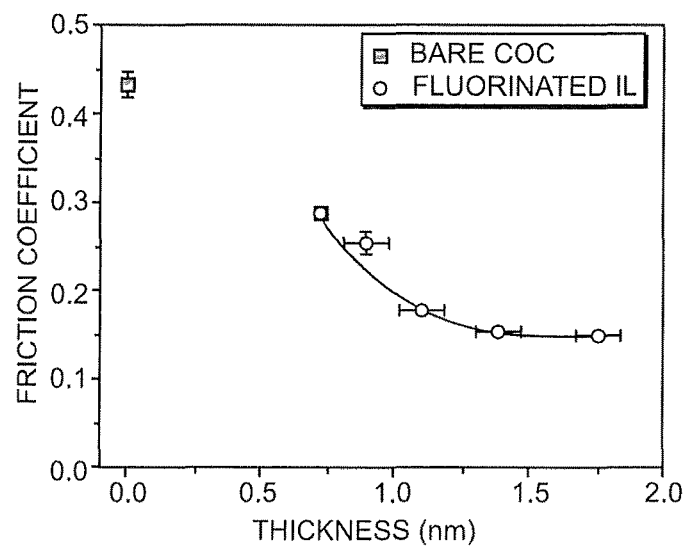
FIG. 14 shows friction results of the nanometer-thick 1-1H,1H,2H,2H-perfluorohexyl-3-methylimidazolium bis(trifluoromethylsulfonyl)imide with varying thicknesses on COC according to preferred methods of the present disclosure.

FIG. 14 presents the friction results of the nanofilms of 1-1H,1H,2H,2H-perfluorohexyl-3-methylimidazolium bis(trifluoromethylsulfonyl)imide. The friction of the bare COC surface is used as control. The friction coefficients of the nanometer-thick lubricants consisting of the highly fluorinated IL of the present disclosure reached minimum values of ~0.15 when the nanofilms were thicker than the ML thickness of the highly fluorinated IL.

Example 2

FIG. 15 shows the synthetic path of 1-1H,1H,2H,2H-perfluorohexyl-3-2-hydroxylethylimidazolium bis(trifluoromethylsulfonyl)imide. Initially, 21.8 mmol 1-Iodo-1H,1H,2H,2H-perfluorohexane was dissolved in 35 mL Toluene. 24.0 mmol 1-(2-hydroxyethyl)imidazole was added, and the reaction is refluxed at 110° C. under $N_2$ purging for 15 hr. The first step of the synthesis undergoes a $S_N2$ reaction. After cooling to RT, Toluene was decanted. The remaining wax was stirred in 200 mL diethyl ether. The wax was washed with 2×150 mL diethyl ether and dried under vacuum overnight. The solid product was then dissolved in 80 mL DI water at 65° C. 21.8 mmol lithium bis(trifluoromethane)sulfonimidate was then added, and the reaction was stirred for 3 hr. The second step of the synthesis undergoes a metathesis reaction. Afterwards, the product was dissolved in 200 mL ethyl acetate and washed with 4×100 mL DI water until pH 6-7. The test on F with $AgNO_3$ in the separated water phase was negative. Finally, the final product was extracted from the solvent by rotary evaporation and dried under vacuum at 75° C. overnight. The synthesized 1-1H,1H,2H,2H-perfluorohexyl-3-2-hydroxylethylimidazolium bis(trifluoromethylsulfonyl)imide was a viscous liquid.

Figure 17:
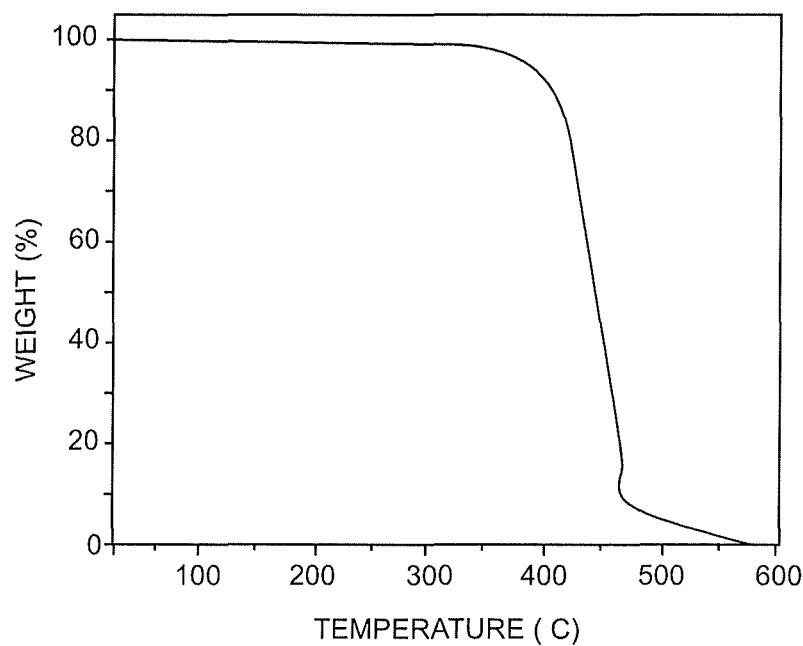
FIG. 17 shows TGA results of 1-1H,1H,2H,2H-perfluorohexyl-3-2-hydroxyethylimidazolium bis(trifluoromethylsulfonyl)imide synthesized according to a preferred method of the present disclosure.

$^1$H NMR was conducted on the obtained 1-1H,1H,2H,2H-perfluorohexyl-3-2-hydroxylethylimidazolium bis(trifluoromethylsulfonyl)imide. The spectrum and all the peak assignments are indicated in FIG. 16, which demonstrates the successful synthesis. Moreover, the TGA result in FIG. 17 shows only one step of weight loss, which indicates the excellent thermal stability of the highly fluorinated IL. The surface tension reduces to 24.8 mN/m based on the pendant drop analysis, as compared to the 30.8 mN/m surface tension for the commercially available 1-hexyl-3-methylimidazolium bis(trifluoromethylsulfonyl)imide.

Figure 18:
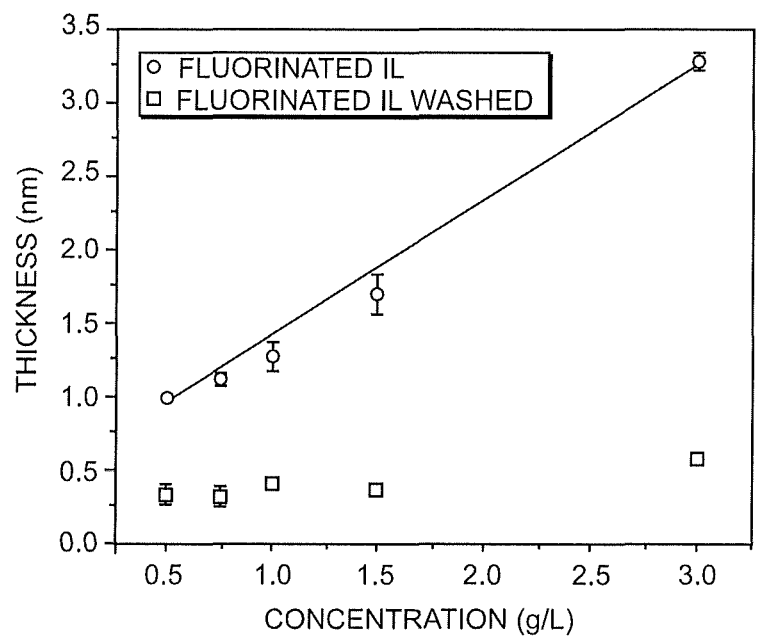
FIG. 18 shows nanofilm thicknesses of 1-1H,1H,2H,2H-perfluorohexyl-3-2-hydroxyethylimidazolium bis(trifluoromethylsulfonyl)imide on COC at various concentrations before and after Vertrel XF washing according to preferred methods of the present disclosure.

Nanometer-thick films of 1-1H,1H,2H,2H-perfluorohexyl-3-2-hydroxylethylimidazolium bis(trifluoromethylsulfonyl)imide was applied on the COC surfaces by the preferred fabrication method of the current disclosure. As shown in FIG. 18, the thickness of the fabricated nanofilms increases proportionally with the concentration of the bulk solutions within the investigated thickness range of nanofilm thickness. FIG. 18 also shows that ~0.4-0.5 nm of the highly fluorinated IL nanofilms survived the Vertrel XF washing, indicating enhanced bonding interactions between the nanofilms and the solid substrates.

Figure 19:
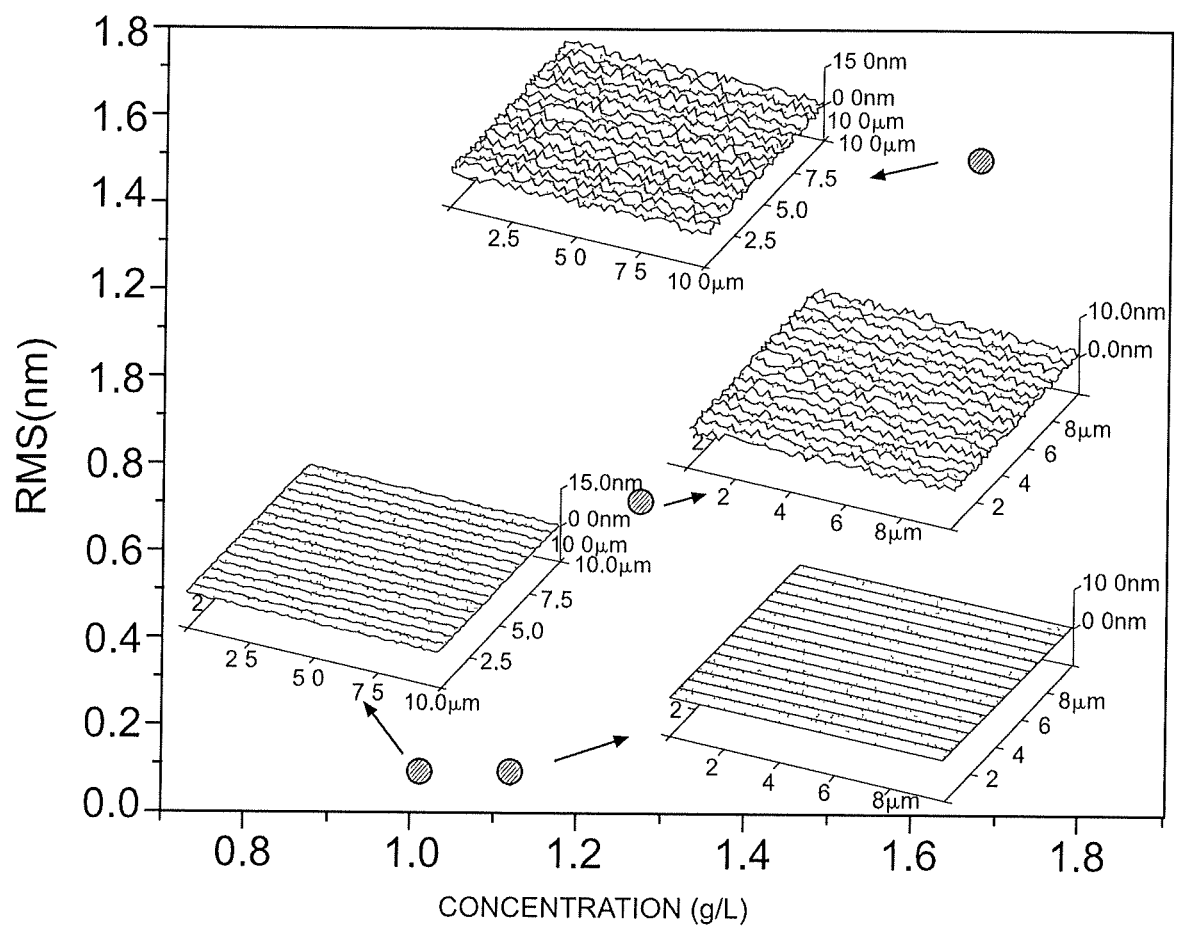
FIG. 19 shows surface roughness results of the nanometer-thick 1-1H,1H,2H,2H-perfluorohexyl-3-2-hydroxyethylimidazolium bis(trifluoromethylsulfonyl)imide with varying thicknesses on COC according to preferred methods of the present disclosure.

ML thickness of the obtained 1-1H,1H,2H,2H-perfluorohexyl-3-2-hydroxylethylimidazolium bis(trifluoromethylsulfonyl)imide was determined by AFM surface roughness analysis. FIG. 19 shows the surface roughness results and the corresponding AFM images of the highly fluorinated IL with varying thicknesses on COC. The surface roughness results revealed that the nanofilm surfaces remained very smooth when the nanofilms were thinner than ~1.1 nm, while the nanofilm surfaces became much rougher when the nanofilms were thicker than ~1.1 nm. As a result, 1.1 nm is determined to be the ML thickness for 1-1H,1H,2H,2H-perfluorohexyl-3-2-hydroxylethylimidazolium bis(trifluoromethylsulfonyl)imide. This highly fluorinated IL of the present disclosure has the potential to achieve extremely low ML thickness because of its small molecular size.

Figure 20:
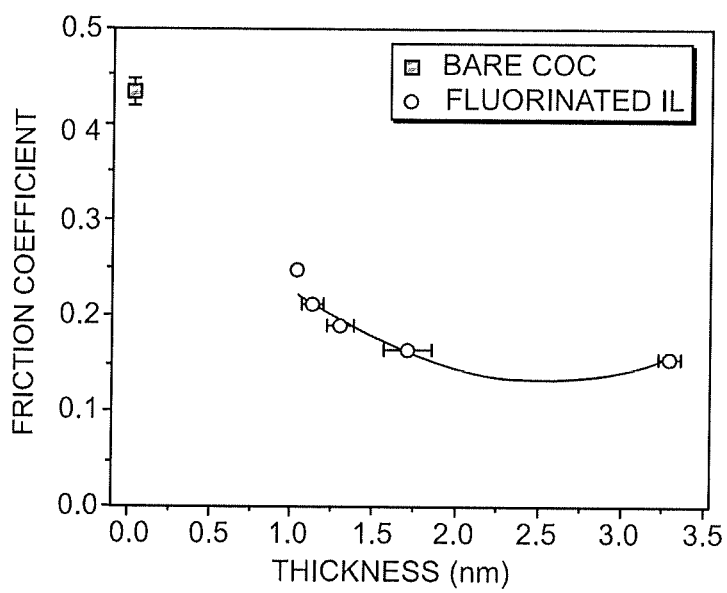
FIG. 20 shows friction results of the nanometer-thick 1-1H,1H,2H,2H-perfluorohexyl-3-2-hydroxyethylimidazolium bis(trifluoromethylsulfonyl)imide with varying thicknesses on COC according to preferred methods of the present disclosure.

FIG. 20 shows the friction results of the nanometer-thick 1-1H,1H,2H,2H-perfluorohexyl-3-2-hydroxylethylimidazolium bis(trifluoromethylsulfonyl)imide. The friction of the bare COC surface is used as control. The friction coefficients of the nanometer-thick lubricants consisting of the highly fluorinated IL of the present disclosure approached minimum values of ~0.15 when the nanofilms grew thicker than the ML thickness of the highly fluorinated IL.

What is claimed is:

1. An ionic liquid comprising:
   a cation (or conjugate acid), wherein the cation (or conjugate acid) is represented by General Formula (A) below or General Formula (B) below or General Formula (C) or General Formula (D) below or General Formula (E):

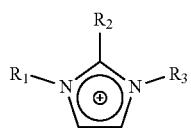

General Formula (A)

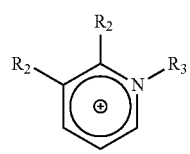

General Formula (B)

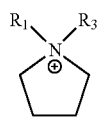

General Formula (C)

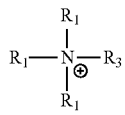

General Formula (D)

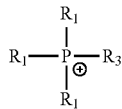

General Formula (E)

wherein $R_1$ represents $CH_2CH_2(CF_2)_nCF_3$, where n is an integer ranging from 0 to 7, or an alkyl chain $CH_3$, or $CH_2OH$, or $CH_2CH_2OH$; $R_2$ represents $CH_2CH_2(CF_2)_nCF_3$, where n is an integer ranging from 0 to 7, or a hydrogen atom H, or $CH_2OH$, or $CH_2CH_2OH$; and $R_3$ represents $CH_2CH_2(CF_2)_nCF_3$, where n is an integer ranging from 0 to 7; and an anion (or conjugate base) comprising bis(trifluoromethanesulfonimide) or tris(pentafluoroethyl)trifluorophosphate or an anion (or conjugate base), wherein the anion (or conjugate base) is represented by General Formula (Z) below:

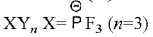

$XY_n \; X=\overset{\ominus}{P}F_3 \; (n=3)$ $Y=(CF_2)_mCF_3 \; (m=0, 1, 2, \ldots)$  General Formula (Z)

wherein X represents $PF_3$ with "n" equaling 3; and wherein Y represents $(CF_2)_mCF_3$ with "m" equaling 0, 1, 2, 3, 4, 5 or 6.

2. A lubricant comprising: the ionic liquid according to claim 1.

3. A magnetic recording medium comprising:
   a non-magnetic support;
   a magnetic layer on the non-magnetic support; and
   the lubricant according to claim 1 on the magnetic layer.

4. The magnetic recording medium of claim 3, wherein the magnetic layer has a carbon overcoat and the lubricant is disposed on the carbon overcoat of the magnetic layer.

5. A method of applying an ionic liquid on a surface of a solid substrate, such as a magnetic media with a carbon overcoat, comprising:
   providing the ionic liquid which comprise the ionic liquid of claim 1;
   preparing a dilute solution by dissolving the ionic liquid in 2,3-dihydrodecafluoropentane;
   dipping the solid substrate into the dilute solution vertically at a first rate of travel (mm/min); and
   withdrawing the solid substrate vertically from the dilute solution at a second rate of travel (mm/min).

6. The method of claim 5, wherein the first rate of travel equals the second rate of travel.

7. The method of claim 5 wherein each of the first rate of travel and the second rate of travel equals 60 mm/min.

8. The method of claim 5, wherein the first rate of travel is not equal to the second rate of travel.

* * * * *